US011346849B2

(12) United States Patent
Meier

(10) Patent No.: US 11,346,849 B2
(45) Date of Patent: May 31, 2022

(54) METHODS FOR THE PREDICTION, PROGNOSIS, AND/OR DIAGNOSIS OF AN INFLAMMATORY RESPONSE ASSOCIATED WITH SCHIZOPHRENIA

(71) Applicant: Ute-Christiane Meier, Munich (DE)

(72) Inventor: Ute-Christiane Meier, Munich (DE)

( * ) Notice: Subject to any disclaimer, the term of this patent is extended or adjusted under 35 U.S.C. 154(b) by 453 days.

(21) Appl. No.: 14/899,546

(22) PCT Filed: Jun. 17, 2014

(86) PCT No.: PCT/IB2014/062299
§ 371 (c)(1),
(2) Date: Dec. 17, 2015

(87) PCT Pub. No.: WO2014/203164
PCT Pub. Date: Dec. 24, 2014

(65) Prior Publication Data
US 2016/0131666 A1    May 12, 2016

(30) Foreign Application Priority Data

Jun. 17, 2013  (GB) ...................... 1310734

(51) Int. Cl.
*G01N 33/82* (2006.01)
*G01N 33/68* (2006.01)
*H01J 49/00* (2006.01)

(52) U.S. Cl.
CPC ......... *G01N 33/82* (2013.01); *G01N 33/6893* (2013.01); *H01J 49/0036* (2013.01); *G01N 2333/5421* (2013.01); *G01N 2333/96494* (2013.01); *G01N 2800/7095* (2013.01)

(58) Field of Classification Search
CPC ......... G01N 33/82; G01N 2333/96494; G01N 2800/7095
See application file for complete search history.

(56) References Cited

U.S. PATENT DOCUMENTS

2012/0195984 A1    8/2012    Lombard

FOREIGN PATENT DOCUMENTS

| WO | WO2012/094550 | * | 7/2012 |
| WO | 2012129650 | | 10/2012 |
| WO | WO2013/040419 | * | 3/2013 |

OTHER PUBLICATIONS

Deluca, G.C. et al. Review: The role of vitamin D in nervous system health and disease. Neuropathology and Applied Neurobiology, 2013, 39:458-484.*
Domenici E., et al. Plasma protein biomarkers for depression and schizophrenia by multi-analyte profiling of case-control collections. PLoS One, 2010, 5(2):e9166, p. 1-12.*
Humble M.B., et al. Low serum levels of 25-hydroxyvitamin D (25-OHD) among psychiatric out-patients in Sweden: Relations wiht season, age, ethnic origin and psychiatric diagnosis. J. Steroid Biochem. Mol. Biol., 2010, 121:467-470.*
Keller, W.R., et al. A review of anti-inflammatory agents for symptoms of schizophrenia. J. Psuchopharmacol., 2013, 27(4):337-342.*
Leppert, D., et al. Matrix metalloproteinase-9 (gelatinase B) is selectively elevated in CSF during relapses and stable phases of multiple sclerosis. Brain, 1998, 121:2327-2334.*
Zhang, X.Y., et al. Elevated interleukin-2, interleukin-6 and interleukin-8 serum levels in neuroleptic-free schizophrenia: association with psychopathology. Schizophrenia Research, 2002, 57:247-258.*
Goodison, S., et al. A multi-analyte assay for the non-invasive detection of bladder cancer. PLoS One, 2012, 7(10):e47469, p. 1-6.*
Van den Ouweland J.M.W., et al. Vitamin D and metabolites measurement by tandem mass spectrometry. Rev. Endocr. Metab. Disord., 2013, 14:159-184.*
Kim T.N. et al. "Relationships between sarcopenic obesity and insulin resistance inflammation, and vitamin D status: the Korean Sarcopenic Obsity Study." Apr. 12, 2003.
Azali, P et al., Low serum levels of vitamin D in idipathic inflammatory myopathies.
Coussens, A K et al., Vitamin D accelerates resolution of inflammatory response during tuberculosis treatment.
ISR and WO as issued in PCT/IB2014/062299, dated Oct. 1, 2014.

* cited by examiner

*Primary Examiner* — Dong Jiang
(74) *Attorney, Agent, or Firm* — Fresh IP PLC; Clifford D. Hyra; Aubrey Y. Chen

(57) ABSTRACT

An in-vitro method for the prediction, prognosis and/or diagnosis of an inflammatory response associated with a condition or disease such as schizophrenia in a subject, the method comprising determining in a sample of a subject the level of 25-hydroxy vitamin D3, preferably in combination with the level of least one biomarker wherein the at least one biomarker is selected from innate chemokine (IL-8) and matrix metalloproteinase (MMP-9); and comparing the levels of said 25-hydroxy vitamin D3 and at least one biomarker to a control level of 25-hydroxy vitamin D3 and the at least one biomarker respectively in order to determine a positive or negative prediction, prognosis and/or diagnosis of said inflammatory response indicating an associated condition or disease, such as schizophrenia.

2 Claims, 2 Drawing Sheets

METHODS FOR THE PREDICTION, PROGNOSIS, AND/OR DIAGNOSIS OF AN INFLAMMATORY RESPONSE ASSOCIATED WITH SCHIZOPHRENIA

FIELD OF THE INVENTION

The present invention relates to a combinatorial biomarker assay for assessing inflammatory/immunological processes, particularly but not exclusively in schizophrenia and/or multiple sclerosis.

BACKGROUND OF THE INVENTION

Schizophrenia is a chronic severe psychiatric disorder that afflicts over 50 million people worldwide. Its major clinical features include thought disorders, auditory and visual hallucinations, delusions, social withdrawal, lack of motivation, and cognitive dysfunction. Its aetiology is unknown, but it is now proving to be multi-factorial, with diverse genetic and environmental contributions. Identification of risk factors should hold important clues to novel preventive and therapeutic strategies. Several aetiological theories have been proposed involving developmental or neurodegenerative processes, neurotransmitter abnormalities, infections, immune dysfunction and/or autoimmune mechanisms (1).

Evidence for contributions from the immune system comes from genome-wide association studies finding association with the major histocompatibility complex (MHC) region to schizophrenia (2).

Infection is one of the suspected risk factors for schizophrenia. The first response to infection is mounted by the innate immune system and inflammation is a key part. Innate immune responses comprise several reactions that isolate and destroy the invading pathogen. Pathogen-associated molecular patterns (PAMPs) are recognized by pattern recognition receptors (PRRs), which are expressed on antigen-presenting cells as proposed by Janeway in 1989 (12). The receptors include Toll-like receptors (TLRs), retinoic acid inducible gene (RIG-I)-like and nucleoside oligomerisation domain (NOD)-like receptors. TLR-3, -7 and -9 recognise microbial patterns inside infected cells, whereas TLR-2, -4 and -5 recognise bacterial patterns on cell surfaces. Once stimulated, these receptors activate signalling pathways, which initiate the secretion of innate chemokines/cytokines and help mount successful tailor-made adaptive anti-pathogen responses.

Early childhood infections of the brain increase schizophrenia risk ~5-fold (4, 5). Even during pregnancy, particularly the second trimester, infections correlate with an increased risk to offspring later in life (5, 6). Several infections have been studied during pregnancy such as rubella, influenza and toxoplasma (7). Injecting pregnant mice with synthetic double-stranded DNA poly I:C, to mimic viral infections/interferon responses, and lipopolysaccharide (LPS), a highly inflammatory component of bacterial cell walls, elicited morphological and behavioral changes characteristic of the brain in schizophrenia (8-11); however, the underlying mechanisms of this change are not fully understood.

Interestingly, fetal exposure to the innate chemokine IL-8, which is part of the innate acute phase response, correlated significantly with schizophrenia risk in offspring (13). In addition, IL-8 levels in mothers during the second trimester of pregnancy correlated significantly with increased schizophrenia risk in a prospective birth cohort study (14). Fetal exposure to elevated IL-8 triggered structural neuroanatomic alterations, e.g. significant increases in ventricular cerebrospinal fluid, and significantly decreased volumes of the left entorhinal and the right posterior cingulate cortex (15). Elevated IL-8 levels have also been described in untreated schizophrenic patients ex vivo and upon stimulation with LPS (16).

IL-8 is known to induce the expression of matrix metalloproteinase-9 (MMP-9) in vitro (17), changes in which are implicated in schizophrenia, Alzheimer's disease, vascular dementia and also in multiple sclerosis, cancer and heart disease. A recent multi-analyte analysis of case-control collections found elevated MMP-9 levels in schizophrenia, which were not altered by neuroleptic treatment and may therefore represent a "trait" marker (18). Furthermore, recent genotyping studies showed associations with a functional polymorphism (-1562C/T) of the MMP-9 gene in schizophrenia (19), which was confirmed in a Chinese cohort (20), though not in a family-based association study (21). Interestingly, the same MMP-9 polymorphism may also influence susceptibility to MS, where serum MMP-9 levels correlate with MRI-documented disease activity in relapsing-remitting disease (RRMS). The extracellular proteolytic system comprises metallo-proteinases and their endogenous tissue inhibitors (TIMPs). Some MMPs can process several of the proteins involved in synaptogenesis, synaptic plasticity, and long-term potentiation (22). MMP-9 regulates synaptic plasticity in the hippocampus in vitro (23,24), and the ratio of TIMP-1 and MMP-9 reportedly modulates learning and memory processes (25). Altered plasma MMP-9 levels have also been described in Alzheimer's disease and vascular dementia (26). Interestingly, the same MMP-9 polymorphism also influenced susceptibility to MS (27), where serum MMP-9 levels correlated with MRI-documented disease activity in relapsing-remitting disease (RRMS) (28).

MMP-9 may also play a role in defense against pathogens, where stimulation with poly I:C leads to significant up-regulation of MMP-9 levels in epithelial cells (29). In addition, MMP-9, and TIMP-1 were significantly higher in patients with HHV-6 encephalitis (30). MMP-9 levels are also correlated with progressive liver damage in HBV and HCV infection (31). Furthermore, MMP-9 is critical for effective bacterial phagocytosis of Streptococcus pneumoniae and reactive oxygen species generation in neutrophils (32). Stimulation of Toll-like receptor-4 with bacterial LPS increases MMP-9 expression in fibroblasts (33).

Of particular interest is the finding that MMP-9 gene expression, secretion and activity is significantly inhibited by vitamin-D in M tuberculosis infection (34). Vitamin-D is produced by skin exposure to ultraviolet B (UVB) solar radiation. UVB converts 7-dehydrocholesterol precursors into previtamin D3, which spontaneously changes to vitamin-D3 (VitD3). VitD3 is converted into 25-hydroxyvitamin D3 (25-OHD) and its final active form, 1,25-dihydroxyvitamin D3 (1,25-OHD). Interestingly, there is an excess of schizophrenia patients born from January to March (35, 36), which might reflect maternal hypovitaminosis-D (37, 38), and/or maternal infection during pregnancy. A further study also identified a >10 fold variation in schizophrenia prevalence and a tendency for prevalence to increase with latitude (39), just as for MS, where VitD3 is also implicated (40). A recent case-control study on neonatal blood samples identified a significant association between neonatal vitamin-D status and risk of schizophrenia (41). In adult women, high intake of vitamin-D and fish correlated with a lower rate of psychotic-like symptoms (42). However, no significant association was detected between four vitamin-D receptor single nucleotide polymorphisms and the risk of schizophrenia (43). Nevertheless, low serum levels of 25-OHD were reported among a psychiatric out-patient cohort in Sweden. In the Swedish schizophrenia cohort, the median 25-OHD was 45 nmol/l—considerably lower than reported for healthy Swedish subjects. Only 14.5% had recommended levels of 25-OHD (>75 nmol/l). Hypovitaminosis-D was present in 56.5% of schizophrenia patients (levels<50 nmol/l) (44).

Currently, schizophrenia diagnosis is based on a clinician's ability to make inferences about patients' inner experiences as no laboratory tests are available that aid in diagnosis, inform treatment strategies or help monitor and predict treatment response. Detrimental comorbidities include metabolic syndrome, other cardiovascular risk factors and diabetes mellitus. Efficient biomarker discovery and assaying techniques are therefore paramount, and will facilitate the future development of patient stratification and personalized medicine strategies.

Current treatments target neurotransmitter pathways in the brain. Antipsychotics act predominantly as dopamine D2 receptor antagonists, and target the symptoms but not the underlying cause of the disease. However, the exact mechanism leading to dopaminergic dysfunction in schizophrenia remains unknown. Recent findings highlight the role of inflammation as an important player in dysregulation of the neurotransmitter system. As bacterial and viral infections are triggers of inflammatory responses, they are potential culprits in at least a subgroup of schizophrenia patients.

SUMMARY OF THE INVENTION

The inventors have identified a set of analytes as candidate blood-based biomarker signatures for schizophrenia, which mirror the existence of dysregulated immune/inflammatory responses. They have surprisingly found interdependence between the inflammatory response in schizophrenia and 25-hydroxyvitamin D and that low serum levels of 25-hydroxyvitamin-D3 can be used as a biomarker of inflammation. Furthermore, they claim that measuring several putative inflammatory biomarkers simultaneously as a combinatorial biomarker of active inflammation can significantly enhance diagnostic accuracy of the test in comparison to the measurement of a single biomarker and offer intervention strategies. The analyte markers may comprise additional cytokines/chemokines and Vitamin-D metabolites.

This invention highlights a novel and unique test to monitor peripheral inflammatory status using a combinatorial biomarker.

The present invention will allow monitoring of peripheral inflammation, and means of modulation in schizophrenia, other psychiatric/neurological and non-psychiatric/neurological conditions, e.g. mood disorders, Tourette syndrome, autism, Alzheimer's disease, amyotrophic lateral sclerosis, dementia, Parkinson's disease, multiple sclerosis in addition to persistent bacterial and viral infections, neuroAIDS, diabetes, metabolic syndrome, asthma, psoriasis, ulcerative colitis, rheumatoid arthritis and other autoimmune conditions, heart disease and cancer.

In the first aspect the invention provides an in vitro method for the prediction, prognosis or diagnosis of an inflammatory response associated with a particular disease or condition in a subject, the method comprising determining in a biological sample of a subject the level of vitamin D3, preferably 25-hydroxyvitamin D3; and comparing the levels of said vitamin D3, preferably 25-hydroxyvitamin D3 to a control level of vitamin D3, preferably 25-hydroxyvitamin D3 in order to determine a positive or negative prediction, prognosis or diagnosis of said inflammatory response associated with a disease or condition.

Preferably, the in vitro method is used to monitor peripheral inflammation. More preferably, the method provides for the prediction, prognosis or diagnosis of a condition or disease associated with a peripheral inflammatory response, such as those selected from the group consisting of schizophrenia, mood disorders, Tourette syndrome, autism, Alzheimer' disease, amyotrophic lateral sclerosis, dementia, Parkinson's disease, multiple sclerosis and other psychiatric/neurological and non-psychiatric/neurological conditions, neuroAIDS, diabetes, metabolic syndrome, asthma, psoriasis, ulcerative colitis, rheumatoid arthritis and other autoimmune conditions, heart disease and cancer, preferably being schizophrenia and multiple sclerosis, especially schizophrenia.

More preferably, the method comprises determining in the biological sample the level of at least one biomarker in addition to the level of vitamin D3, preferably 25-hydroxyvitamin D3, and comparing the level of the at least one biomarker to a control level of the biomarker in order to determine a positive or negative prediction, prognosis or diagnosis of said inflammatory response. In particular, the at least one biomarker is a cytokine or chemokine, more preferably the biomarker is selected from innate chemokine (IL-8) and matrix metalloproteinase (MMP-9).

A specific embodiment of the invention provides a method for monitoring disease activity/occurrence of comorbidities in schizophrenia comprising measuring vitamin D3, especially 25-hydroxyvitamin D3 level in a biological sample from a subject in combination with the levels of either or both IL-8 and MMP-9 in the biological sample.

Preferably, the level of 25-hydroxyvitamin D3 indicative of a positive diagnosis is equal to or less than 75 nmol/L, more preferably equal to or less than 50 nmol/L. The level of IL-8 is preferably at least 20 pg/ml, more preferably above 32 pg/ml compared to a control level below these values. The level of MMP-9 is preferably above 700 ng/ml, more preferably above 705 ng/ml compared to a control level below these values.

The invention also provides a method for determining the efficacy of a treatment regimen for treating an inflammatory response, in particular schizophrenia and/or multiple sclerosis, in a subject by comparing the levels of 25-hydroxyvitamin D3 in a biological sample from the subject, preferably in combination with the levels of least one biomarker wherein the at least one biomarker is selected from IL-8 and MMP-9 in the biological sample before, during and after treatment, wherein said treatment is considered efficient if the level of 25-hydroxyvitamin D3 and/or IL-8 or MMP-9 is approaching a predetermined control level for the 25-hydroxyvitamin and/or IL-8 and/or MMP-9.

It is to be appreciated that determination of an efficient treatment is recognised by measuring a level of 25-hydroxyvitamin D3 that is above 50 nmol/L, preferably above 75 nmol/L relative to an initial measurement prior to treatment outside this range. The level of IL-8 is preferably below 20 pg/ml and the level of MMP-9 is preferably 700 ng/ml, preferably in the range 169-705 ng/ml, relative to an initial measurement prior to treatment that is outside this range Another specific embodiment of the invention also provides a method for assessing the efficacy of a treatment regimen for treating schizophrenia/monitoring of the occurrence of comorbidities in a subject by comparing the levels of 25-hydroxyvitamin D3 in a biological sample from the subject in combination with the levels of IL-8 and MMP-9 in the biological sample before, during and after treatment.

The present invention also provides a method for establishing a reference biomarker profile comprising the steps of (a) determining a quantity of vitamin D3, preferably 25-hydroxyvitamin D3 and at least one biomarker selected from IL-8 and MMP-9 in a sample obtained from a healthy subject or a subject having an inflammatory response, especially having schizophrenia or multiple sclerosis; and (b) storing the quantity of the 25-hydroxyvitamin D3 and selected biomarker in a reference biomarker profile respectively for healthy subjects or subjects having an inflammatory response, especially having schizophrenia or multiple sclerosis.

The invention also relates to a kit comprising means for detecting the level of 25-hydroxyvitamin D3 in a biological sample from a subject, preferably in combination with the level of at least one biomarker wherein the at least one biomarker is selected from IL-8 and MMP-9. The kit comprises appropriate detection reagents and optionally further additives.

An embodiment of the invention provides a kit comprising means for detecting the level of 25-hydroxyvitamin D3 in a biological sample from a subject in combination with the levels of IL-8 and MMP-9 in the biological sample.

In particular embodiments, the biological sample comprises serum, plasma, whole blood, saliva or urine. More preferably, the sample comprises serum.

The subject is preferably a human subject and may or may not be diagnosed with a condition associated with a peripheral inflammatory response, in particular schizophrenia.

The invention provides a rationale for down-regulating the inflammatory response by vitamin-D3 supplementation to counteract hypovitaminosis-D. Inflammation is an important part of the innate immune system and in a subgroup of schizophrenia patients the activation of innate immunity by pathogens such as viruses and bacteria has to be considered and can be targeted by antibiotic or antiviral treatment.

Caren Ramien contributed to the experimental design and execution, data analysis and interpretation. Dr Sreeram Ramagopalan contributed to the data interpretation and analysis.

BRIEF DESCRIPTION OF THE DRAWINGS

The invention will now be described in further detail with reference to the following examples and accompanying figures in which.

DETAILED DESCRIPTION OF THE INVENTION

Example 1

Figure 1:
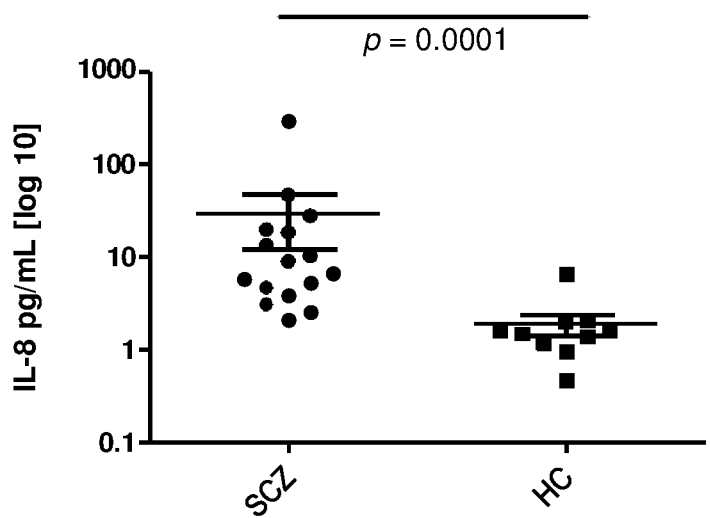
FIG. 1: Serum IL-8 levels in 16 schizophrenia patients (SCZ) and 10 healthy controls (HC), determined by ELISA. The difference between them was significant (29.17+/−17.66 pg/ml versus 1.88+/−0.52 pg/ml, p=0.0001). Data are expressed as means+/−SEM; p-values are derived from a two-tailed Mann-Whitney test.

Investigation Observing Significantly Higher Levels of IL-8 in Schizophrenia Patients than in Healthy Controls To investigate the potential role of the innate immune system in the pathophysiology of schizophrenia, we tested for an altered innate immune/inflammatory signature(s) in patients' blood. As we had found elevated levels of IL-8 in the serum of patients with multiple sclerosis (MS), and in experimental autoimmune encephalomyelitis (EAE) (45) (the animal model of MS), we were interested in the IL-8 status of schizophrenia patients (SCZ). We measured serum levels of IL-8 in SCZ patients and healthy controls (FIG. 1). They were significantly higher in SCZ patients than in healthy controls (p<0.05).

Example 2

Figure 2:
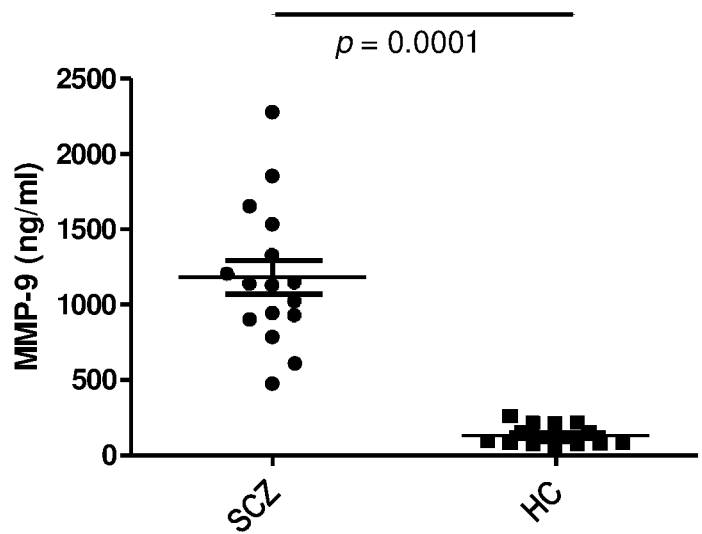
FIG. 2: Serum levels of MMP-9 in SCZ patients and healthy controls (1200+/−120 ng/ml versus 130+/−18 ng/ml, p=0.0001), determined by ELISA. Data are expressed as means+/−SEM; p-values are derived from two-tailed Mann-Whitney test.

Investigations Observed Significantly Elevated MMP-9 in SCZ Patients than in Healthy Controls We initially compared levels of MMP-9 in the serum of SCZ patients and healthy controls. As shown in FIG. 2, the level of MMP-9 in SCZ patients was significantly higher than in healthy controls (FIG. 2, p<0.05).

Example 3

Investigation into Hypovitaminosis-D in SCZ Patients

We next assessed the 25-hydroxyvitamin-D3 status of SCZ patients. Its recommended level is above 75 nmol/L (44) and levels under 50 nmol/L mark deficiency (46). All but one patient were deficient in 25-hydroxyvitamin-D3 (93.75%).

Example 4

Figure 3:
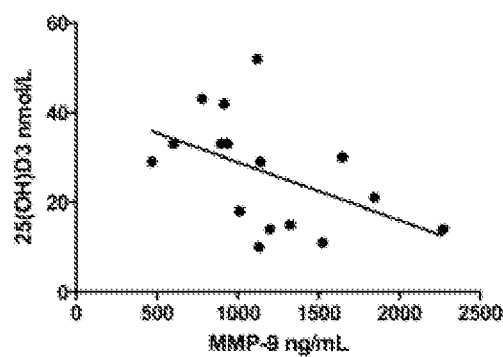
FIG. 3: Correlating MMP-9 and 25-hydroxyvitamin D3 levels in 16 SCZ patients. The regression line is shown. Analysis by Spearman correlation yielded an r-value of −0.58 with p=0.017.

Investigations Observed Significant Inverse Correlation of 25-hydroxyvitaminD3 and MMP-9 Levels in SCZ Patients In healthy controls, 25-hydroxyvitamin-D correlated inversely with circulating MMP-9 (47). In our SCZ patients, we too found a significant inverse correlation (FIG. 3)—though not with IL-8 levels (data not shown).

Screening Assays:

Measurement of MMP-9 and IL-8 Levels:

IL-8/CXCL8 and MMP-9 ELISAs (Qantikine Immunoassays R&D Systems, UK) were performed according to the manufacturer's instructions. SCZ and healthy control samples were run on the same plate to control for inter-assay variation. All assays were performed in duplicate and samples run in two separate assays. Absorbance reading was carried out on a Reader BioTek Synergy HT plate reader.

Measurement of 25-Hydroxyvitamin D3 Levels:

Serum levels of 25-hydroxyvitaminD3 were measured by isotope-dilution liquid chromatography-tandem mass spectrometry as described previously (48).

Statistical Analysis

We used GraphPad Prism (5.00 version for Windows, GraphPad Software, San Diego Calif. USA) for all statistical analyses. All analyses conducted used non-parametric tests, including Mann-Whitney tests to evaluate differences between groups, and Spearman rank correlations. P-values less than or equal to 0.05 were considered as statistically significant.

REFERENCES CITED

1. Bown AaP, P. The Origins of Schizophrenia. New York, Chichester, West Sussex: Columbia University Press, 2012.
2. Moises H W, Yang L, Kristbjarnarson H, et al. An international two-stage genome-wide search for schizophrenia susceptibility genes. Nat Genet 1995; 11:321-324.
3. Koponen H, Rantakallio P, Veijola J, Jones P, Jokelainen J, Isohanni M. Childhood central nervous system infections and risk for schizophrenia. Eur Arch Psychiatry Clin Neurosci 2004; 254:9-13.
4. Gattaz W F, Abrahao A L, Foccacia R. Childhood meningitis, brain maturation and the risk of psychosis. Eur Arch Psychiatry Clin Neurosci 2004; 254:23-26.
5. Buka S L, Tsuang M T, Torrey E F, Klebanoff M A, Bernstein D, Yolken R H. Maternal infections and subsequent psychosis among offspring. Arch Gen Psychiatry 2001; 58:1032-1037.
6. Buka S L, Tsuang M T, Torrey E F, Klebanoff M A, Wagner R L, Yolken R H. Maternal cytokine levels during pregnancy and adult psychosis. Brain Behav Immun 2001; 15:411-420.
7. Brown A S. Exposure to prenatal infection and risk of schizophrenia. Front Psychiatry 2011; 2:63.
8. Zuckerman L, Weiner I. Post-pubertal emergence of disrupted latent inhibition following prenatal immune activation. Psychopharmacology (Berl) 2003; 169:308-313.
9. Meyer U, Feldon J. To poly(I:C) or not to poly(I:C): advancing preclinical schizophrenia research through the use of prenatal immune activation models. Neuropharmacology 2012; 62:1308-1321.
10. Baharnoori M, Bhardwaj S K, Srivastava L K. Neonatal behavioral changes in rats with gestational exposure to lipopolysaccharide: a prenatal infection model for developmental neuropsychiatric disorders. Schizophr Bull 2012; 38:444-456.
11. Bitanihirwe B K, Peleg-Raibstein D, Mouttet F, Feldon J, Meyer U. Late prenatal immune activation in mice leads to behavioral and neurochemical abnormalities relevant to the negative symptoms of schizophrenia. Neuropsychopharmacology 2010; 35:2462-2478.
12. Janeway C A, Jr., Medzhitov R. Innate immune recognition. Annu Rev Immunol 2002; 20:197-216. Epub 2001 October 2004.
13. Brown A S, Begg M D, Gravenstein S, et al. Serologic evidence of prenatal influenza in the etiology of schizophrenia. Arch Gen Psychiatry 2004; 61:774-780.
14. Brown A S, Hooton J, Schaefer C A, et al. Elevated maternal interleukin-8 levels and risk of schizophrenia in adult offspring. Am J Psychiatry 2004; 161:889-895.
15. Ellman L M, Deicken R F, Vinogradov S, et al. Structural brain alterations in schizophrenia following fetal exposure to the inflammatory cytokine interleukin-8. Schizophr Res 2010; 121:46-54.
16. Reale M, Patruno A, De Lutiis M A, et al. Dysregulation of chemo-cytokine production in schizophrenic patients versus healthy controls. BMC Neurosci 2011; 12:13.
17. Thirumangalakudi L, Yin L, Rao H V, Grammas P. IL-8 induces expression of matrix metalloproteinases, cell cycle and pro-apoptotic proteins, and cell death in cultured neurons. J Alzheimers Dis 2007; 11:305-311.
18. Domenici E, Wille D R, Tozzi F, et al. Plasma protein biomarkers for depression and schizophrenia by multi analyte profiling of case-control collections. PloS one 2010; 5:e9166.
19. Rybakowski J K, Borkowska A, Skibinska M, Kaczmarek L, Hauser J. The -1562 C/T polymorphism of the matrix metalloproteinase-9 gene is not associated with cognitive performance in healthy participants. Psychiatr Genet 2009; 19:277-278.
20. Han H, He X, Tang J, et al. The C(-1562)T polymorphism of matrix metalloproteinase-9 gene is associated with schizophrenia in China. Psychiatry Res 2011; 190:163-164.
21. Groszewska A, Kapelski P, Skibinska M, Hauser J. Family based association study of MMP-9 gene-1562C>T polymorphism in schizophrenia. Psychiatr Pol 2011; 45:317-324.
22. Ethell I M, Ethell D W. Matrix metalloproteinases in brain development and remodeling: synaptic functions and targets. J Neurosci Res 2007; 85:2813-2823.
23. Bozdagi O, Nagy V, Kwei K T, Huntley G W. In vivo roles for matrix metalloproteinase-9 in mature hippocampal synaptic physiology and plasticity. J Neurophysiol 2007; 98:334-344.
24. Nagy V, Bozdagi O, Matynia A, et al. Matrix metalloproteinase-9 is required for hippocampal late-phase long-term potentiation and memory. J Neurosci 2006; 26:1923-1934.
25. Chaillan F A, Rivera S, Marchetti E, et al. Involvement of tissue inhibition of metalloproteinases-1 in learning and memory in mice. Behav Brain Res 2006; 173:191-198.
26. Lorenzl S, Buerger K, Hampel H, Beal M F. Profiles of matrix metalloproteinases and their inhibitors in plasma of patients with dementia. Int Psychogeriatr 2008; 20:67-76.
27. La Russa A, Cittadella R, De Marco E V, et al. Single nucleotide polymorphism in the MMP-9 gene is associated with susceptibility to develop multiple sclerosis in an Italian case-control study. J Neuroimmunol 2010; 225:175-179.
28. Waubant E, Goodkin D E, Gee L, et al. Serum MMP-9 and TIMP-1 levels are related to MRI activity in relapsing multiple sclerosis. Neurology 1999; 53:1397-1401.
29. Wang J, Watanabe S, Matsukura S, Suzaki H. Double-stranded RNA poly(I:C) enhances matrix metalloproteinase mRNA expression in human nasal polyp epithelial cells. Acta Otolaryngol Suppl 2009:105-109.
30. Kawamura Y, Sugata K, Ihira M, et al. Different characteristics of human herpesvirus 6 encephalitis between primary infection and viral reactivation. J Clin Virol; 51:12-19.
31. Helaly G F. Differences in circulating MMP-9 levels with regard to viral load and AST:ALT ratio between chronic hepatitis B and C patients. Br J Biomed Sci 2011; 68:38-42.
32. Hong J S, Greenlee K J, Pitchumani R, et al. Dual protective mechanisms of matrix metalloproteinases 2 and 9 in immune defense against *Streptococcus pneumoniae*. J Immunol 2011; 186:6427-6436.

33. Wong Y, Sethu C, Louafi F, Hossain P. Lipopolysaccharide regulation of toll-like receptor-4 and matrix metalloprotease-9 in human primary corneal fibroblasts. Invest Ophthalmol Vis Sci 2011; 52:2796-2803.
34. Coussens A, Timms P M, Boucher B J, et al. 1alpha, 25-dihydroxyvitamin D3 inhibits matrix metalloproteinases induced by *Mycobacterium tuberculosis* infection. Immunology 2009; 127:539-548.
35. Mortensen P B, Pedersen C B, Westergaard T, et al. Effects of family history and place and season of birth on the risk of schizophrenia. N Engl J Med 1999; 340:603-608.
36. Disanto G, Morahan J M, Lacey M V, et al. Seasonal distribution of psychiatric births in England. PloS one 2012; 7:e34866.
37. McGrath J. Hypothesis: is low prenatal vitamin D a risk-modifying factor for schizophrenia? Schizophr Res 1999; 40:173-177.
38. McGrath J. Is it time to trial vitamin D supplements for the prevention of schizophrenia? Acta Psychiatr Scand 2010; 121:321-324.
39. Kinney D K, Teixeira P, Hsu D, et al. Relation of schizophrenia prevalence to latitude, climate, fish consumption, infant mortality, and skin color: a role for prenatal vitamin d deficiency and infections? Schizophr Bull 2009; 35:582-595.
40. Ramagopalan S V, Handel A E, Giovannoni G, Rutherford Siegel S, Ebers G C, Chaplin G. Relationship of UV exposure to prevalence of multiple sclerosis in England. Neurology 2011; 76:1410-1414.
41. McGrath J J, Burne T H, Feron F, Mackay-Sim A, Eyles D W. Developmental vitamin D deficiency and risk of schizophrenia: a 10-year update. Schizophr Bull 2010; 36:1073-1078.
42. Hedelin M, Lof M, Olsson M, et al. Dietary intake of fish, omega-3, omega-6 polyunsaturated fatty acids and vitamin D and the prevalence of psychotic-like symptoms in a cohort of 33,000 women from the general population. BMC Psychiatry 2010; 10:38.
43. Handoko H Y, Nancarrow D J, Mowry B J, McGrath J J. Polymorphisms in the vitamin D receptor and their associations with risk of schizophrenia and selected anthropometric measures. Am J Hum Biol 2006; 18:415-417.
44. Humble M B, Gustafsson S, Bejerot S. Low serum levels of 25-hydroxyvitamin D (25-OHD) among psychiatric out-patients in Sweden: relations with season, age, ethnic origin and psychiatric diagnosis. J Steroid Biochem Mol Biol 2010; 121:467-470.
45. Campbell S J, Meier U, Mardiguian S, et al. Sickness behaviour is induced by a peripheral CXC-chemokine also expressed in multiple sclerosis and EAE. Brain Behav Immun 2010; 24:738-746.
46. Holick M F, Binkley N C, Bischoff-Ferrari H A, et al. Evaluation, treatment, and prevention of vitamin D deficiency: an Endocrine Society clinical practice guideline. J Clin Endocrinol Metab 2011; 96:1911-1930.
47. Timms P M, Mannan N, Hitman G A, et al. Circulating MMP9, vitamin D and variation in the TIMP-1 response with VDR genotype: mechanisms for inflammatory damage in chronic disorders? QJM 2002; 95:787-796.
48. Maunsell Z, Wright D J, Rainbow S J. Routine isotope-dilution liquid chromatography-tandem mass spectrometry assay for simultaneous measurement of the 25-hydroxy metabolites of vitamins D2 and D3. Clin Chem 2005; 51:1683-1690.

The invention claimed is:

1. A method for treating inflammation in a schizophrenia patient, the method comprising:
   (i) measuring the level of vitamin D3 and the level of MMP-9 in a biological sample from a schizophrenia patient;
   (ii) determining that the patient has inflammation if the level of vitamin D3 is below the control level of 75 nmol/L and if the level of MMP-9 is above the control level of 700 ng/ml; and
   (iii) treating the patient having inflammation determined in step (ii) with vitamin D3 supplementation and a treatment for inflammation, and optionally with antibiotic and/or antiviral treatment.

2. The method according to claim 1, wherein the vitamin D3 is 25-hydroxyvitamin D3.

* * * * *